(12) United States Patent
Hahr et al.

(10) Patent No.: US 9,956,109 B2
(45) Date of Patent: May 1, 2018

(54) PENILE CONSTRICTION DEVICE

(75) Inventors: Meike Hahr, Hamburg (DE); Till Muhl, Hamburg (DE)

(73) Assignee: OVO JOINT VENTURE, LLC, Hightstown, NJ (US)

( * ) Notice: Subject to any disclaimer, the term of this patent is extended or adjusted under 35 U.S.C. 154(b) by 204 days.

(21) Appl. No.: 14/426,312

(22) PCT Filed: Sep. 7, 2012

(86) PCT No.: PCT/EP2012/067461
§ 371 (c)(1),
(2), (4) Date: Dec. 28, 2015

(87) PCT Pub. No.: WO2014/037046
PCT Pub. Date: Mar. 13, 2014

(65) Prior Publication Data
US 2016/0106569 A1    Apr. 21, 2016

(51) Int. Cl.
*A61F 5/00* (2006.01)
*A61F 5/41* (2006.01)
(Continued)

(52) U.S. Cl.
CPC ............... *A61F 5/41* (2013.01); *A61H 19/32* (2013.01); *A61H 19/34* (2013.01);
(Continued)

(58) Field of Classification Search
CPC ................. A61F 5/41; A61F 2005/414; A61F 2005/415; A61H 19/30; A61H 19/32; A61H 19/34; A61H 19/50
(Continued)

(56) References Cited

U.S. PATENT DOCUMENTS 4,834,115 A * 5/1989 Stewart ..................... A61F 5/41
                                                            128/842
4,942,886 A * 7/1990 Timmons ............. A61B 17/132
                                                            128/885

(Continued)

FOREIGN PATENT DOCUMENTS

GB        2450779        1/2009
WO    WO2007047169        4/2007

*Primary Examiner* — John Lacyk
(74) *Attorney, Agent, or Firm* — Richard E. Oney; Tiffany & Bosco, P.A.

(57) ABSTRACT

Disclosed is a penile constriction device comprising a body including an aperture (4) for surrounding a penis wherein the aperture (4) defines an inner edge (6,7). According to the present invention an elastic strap (8) is arranged within the aperture (4) or at least in alignment with the aperture (4) wherein the ends of the strap (8) are connected to connection points (10) at the inner edge (6,7) of the aperture (4) or at portions of the body (2) adjacent to the aperture (4), and where in the connection points (10) are positioned opposite to each other relative to the aperture (4) and the length of the strap (8) between its both ends is greater than the distance between the connection points (10) so that the strap (8) is able to be optionally brought into a first position (FIG. 4a) so as to limit the aperture (4) for defining a first aperture cross-section area (4.1) or a second (FIG. 4d) position opposite to the first position relative to the aperture (4) so as to limit the aperture (4) for defining a second aperture cross-section (4.2) area which is larger than the first aperture cross-section area (4.1).

20 Claims, 3 Drawing Sheets

(51) Int. Cl.
   *A61H 19/00* (2006.01)
   *A61H 23/02* (2006.01)
(52) U.S. Cl.
   CPC ... *A61F 2005/414* (2013.01); *A61F 2005/417* (2013.01); *A61H 23/02* (2013.01); *A61H 2201/165* (2013.01)
(58) Field of Classification Search
   USPC .................................................. 600/38–41
   See application file for complete search history.

(56) References Cited

U.S. PATENT DOCUMENTS

| | | | | |
|---|---|---|---|---|
| 5,810,710 A * | 9/1998 | Burgos | ............... | A61F 5/41 600/38 |
| 5,873,813 A * | 2/1999 | Weiss | ............... | A61F 5/41 24/20 R |
| 6,306,080 B1 * | 10/2001 | Mitchell | ............... | A61F 5/41 600/38 |
| 6,659,938 B1 * | 12/2003 | Orlowski | ............... | A61F 5/41 600/38 |
| 2004/0236179 A1 | 11/2004 | Egretier | | |
| 2009/0318755 A1 * | 12/2009 | Adams | ............... | A61F 5/41 600/41 |
| 2014/0179996 A1 * | 6/2014 | Oh | ............... | A61F 5/41 600/41 |

* cited by examiner

PENILE CONSTRICTION DEVICE

The present invention relates to a penile constriction device comprising a body including an aperture for surrounding a penis wherein the aperture defines an inner edge.

Conventional penile constriction devices comprising generally an elastic ring or an elastic ring-shaped portion including an aperture which is adapted to encircle the penis closely adjacent the base thereof and adjacent the user's body are known from the prior art. They act by constricting the flow of blood within the organ in a selective manner so that relatively easy flow of blood into the organ is permitted whereas the return flow of blood out of the organ into the body is restricted. This will result in erection of the organ in many cases, and is also effective in permitting longer retention of an erection once it has been obtained, wherein the penile constriction device will then be effective in retaining the erection as long as may be necessary.

Some penile constriction devices in the prior art comprise a construction which allows an adjustment of the aperture cross-section area or the diameter of the aperture within a certain range so as to adapt the restriction function of the penile constriction device in accordance with the size of the organ and/or the user's needs. However, such adjustable penile constriction devices in the prior art have drawbacks due to difficult handling, complex construction and/or high production costs.

It is an object of the present invention to increase the comfort for the handling of a penile constriction device by providing a simple construction which allows an adjustment of the aperture in a convenient way.

In order to achieve the above and further objects, according to the present invention, there is provided a penile constriction device comprising a body including an aperture for surrounding a penis wherein the aperture defines an inner edge, characterized in that an elastic strap is arranged within the aperture or at least in alignment with the aperture wherein the ends of the strap are connected to connection points at the inner edge of the aperture or at portions of the body adjacent to the aperture, and wherein the connection points are positioned opposite to each other relative to the aperture and the length of the strap between its both ends is greater than the distance between the connection points so that the strap is able to be optionally brought into a first position so as to limit the aperture for defining a first aperture cross-section area or a second position opposite to the first position relative to the aperture so as to limit the aperture for defining a second aperture cross-section area which is larger than the first aperture cross-section area.

Due to the arrangement of an elastic strap within the aperture or at least in alignment with the aperture, the aperture cross-section area can be optionally changed between a first amount (first aperture cross-section area) and a second amount (second aperture cross-section area) which is larger than the first amount. This is achieved by that the length of the strap between its both ends is greater than the distance immediately between the connection points where the ends of the strap are connected at the inner surface of the aperture or at portions of the body adjacent to the aperture. As a result, an internal upsetting pressure occurs within the strap along its lengthwise direction whereby the elastic strap is biased beyond a dead point either to the first position so as to limit the aperture for defining the first aperture cross-section area or to the second position opposite to the first position relative to the aperture so as to limit the aperture for defining the larger second aperture cross-section area. For changing from the one position to the other position the elastic strap is to be manually urged towards the dead point by the user whereby the internal upsetting pressure is increased. After having passed the dead point which lies in the center region of the aperture, the internal upsetting pressure now forces the elastic strap to continue moving towards the other position without the user's aid. In its first position, the elastic strap causes a tight fit by limiting the aperture to the smaller first aperture cross-section area, whereas in its second position the strap causes a more comfort fit by limiting the aperture to the larger second aperture cross-section area. Hence, the fitting intensity can be adjusted accordingly. So, the provision of an elastic strap according to the present invention offers a very simple measure for changing the aperture cross-section area wherein the strap is a simple construction with low production costs and easily to be handled.

Further advantageous embodiments and modifications of the present invention are defined in the dependent claims.

According to a preferred embodiment, the connection points are positioned and the length of the strap between its both ends is dimensioned so that the strap is spaced from the inner surface of the aperture in its first position and essentially contacts the inner edge of the aperture in its second position. This embodiment essentially takes advantage of the maximum aperture cross-section area to be offered by the aperture which is achieved by that in its second position the elastic strap contacts the inner edge of the aperture.

In a further preferred embodiment where both the first and second aperture cross-section areas have essentially a shape of an at least approximate circle, the diameter of the second aperture cross-section area is larger than the diameter of the first aperture cross-section area.

If the aperture has essentially the shape of an at least approximate circle, the connection points are positioned at a virtual line spaced from the diameter of the circle of the aperture so that the arrangement of the strap is not symmetrical, but asymmetrical relative to the circular aperture. Due to such an asymmetrical arrangement of the strap, it is achieved that the one aperture cross-section area is larger than the other one.

If, alternatively, the aperture has essentially the shape of an at least approximate ellipse, the connection points should be positioned at a virtual line spaced from the conjugate diameter of the ellipse so that the arrangement of the strap is not symmetrical, but asymmetrical. Due to such an asymmetrical arrangement of the strap, it is achieved that the one aperture cross-section area is larger than the other one.

According to a preferred modification of the aforementioned embodiment, the virtual line extends parallel to the conjugate diameter of the ellipse.

According to a still further preferred modification of the aforementioned embodiment, the transverse and conjugate diameters of the ellipse are dimensioned so that the second aperture cross-section area has essentially a shape of an at least approximate circle. For achieving this, it is advantageous that the difference of the length between the transverse diameter and the conjugate diameter of the ellipse essentially corresponds to the width of the strap, so that the second aperture cross-section area gets a shape of an at least approximate circle with a diameter corresponding to the conjugate diameter.

In order to further simplify the construction, the body and the strap may form an integral unit.

In a further preferred embodiment, the body comprises a part-ring portion limiting the aperture so that such a part-ring portion forms somewhat like a second ring. According to a modification, the part-ring portion is elastic and stretchable e.g. to be placed behind the testicals.

In a still further preferred embodiment, the body comprises an extended portion which includes vibration means adapted to transfer vibrations to an outer surface of at least the extended portion. During use, the extended portion can be provided so as to head towards a female organ like the clitoris so that the extended portion may hit the organ with each move. According to a modification of this embodiment, the extended portion of the body further includes a battery and an electrical connector for connection of an electrical cable for charging the battery. So, such an extended portion can be advantageously used for accommodation of a battery without affecting the size of the body.

According to a still further preferred embodiment, the body is at least partly made of soft silicone material, since such a material has the advantage to be soft, flexible and hygienic.

In the following, a preferred embodiment according to the present invention will be described with reference to the accompanying drawings in which.

Figure 1:
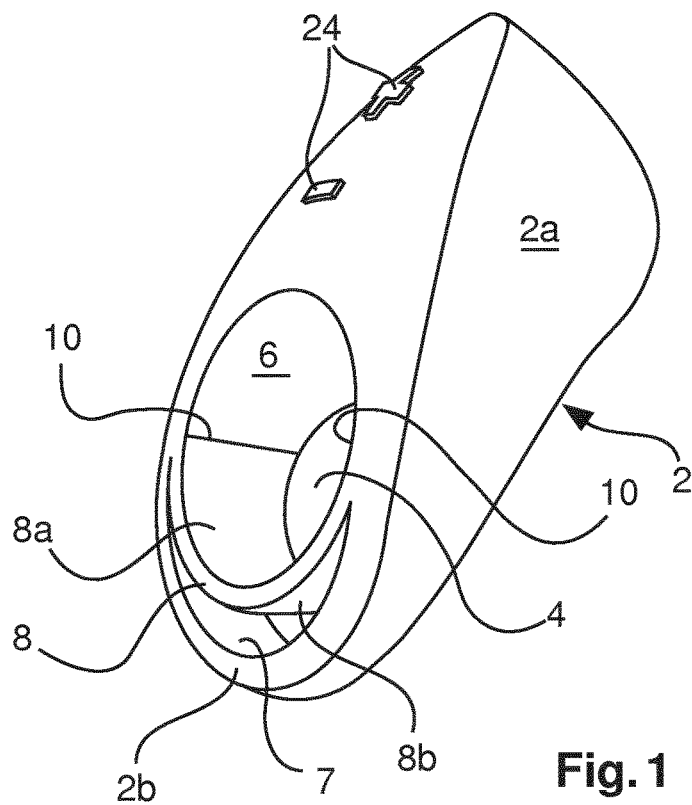
FIG. 1 is a perspective view of a penile constriction ring according to a preferred embodiment of the present invention.
Figure 5:
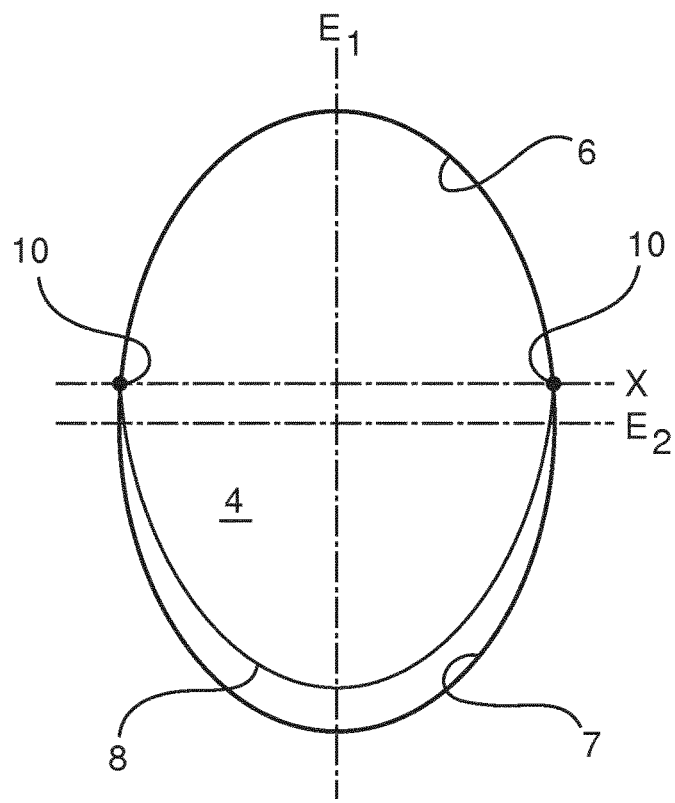
Figures 4A, 4B:
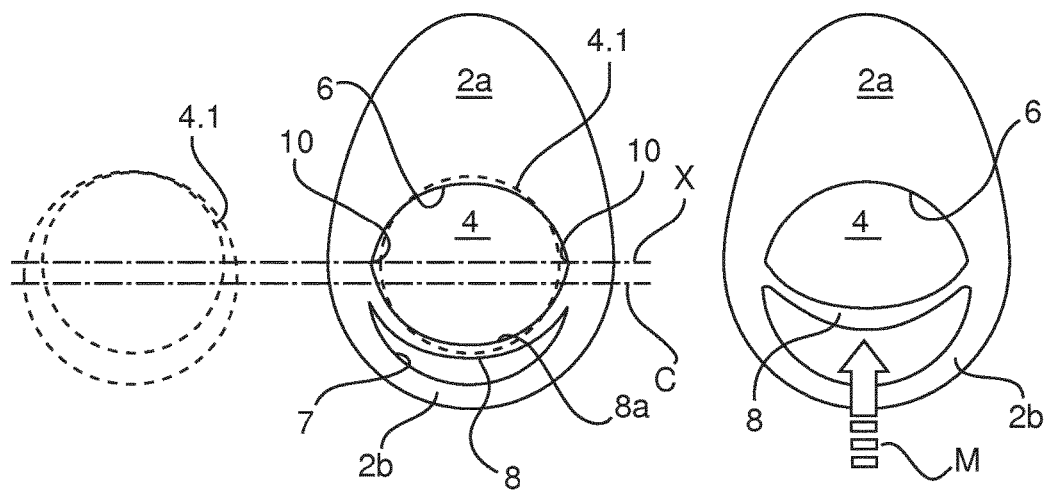
Figures 4C, 4D:
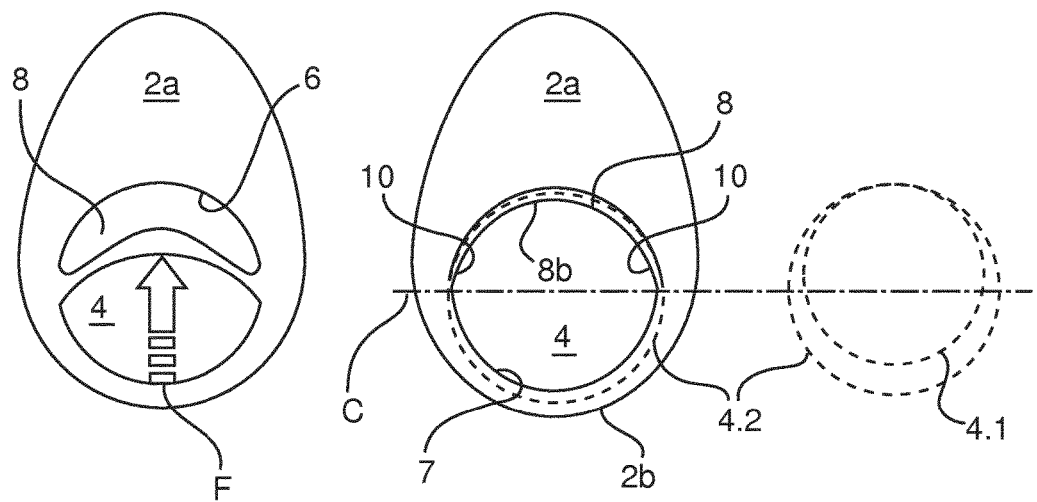

FIGS. 4a to 4d a view upon the penile constriction ring of FIG. 1 with a strap in different positions; and FIG. 5 a sketch schematically showing a further example of the shape of an aperture different from the shape of the aperture shown in FIG. 4.

FIGS. 1 to 4 shows a penile constriction ring according to a preferred embodiment of the present invention which comprises a body 2 having an extended head portion 2a and opposite thereto a part-ring portion 2b. In the embodiment shown in FIGS. 1 to 4, the part-ring portion 2b has an essentially semi circular shape or a shape of an at least approximate semi-circle. Between the head portion 2a and the part-ring portion 2b the body 2 includes an aperture 4 which is provided to encircle a penis when the penile constriction device is used. As in particular shown in FIGS. 1 and 4, the aperture 4 is defined and limited by a first inner surface 6 provided at the head portion 2a and a second inner surface 7 provided at the inner side of the part-ring portion 2b. So, both these first and second inner surfaces 6, 7 commonly form an endless inner edge surrounding the aperture 4.

In the shown embodiment, within the aperture 4 arrangement is an elastic strap 8 whose ends are connected to connection points 10 at the inner edge of the aperture 4 wherein the connection points 10 are positioned opposite to each other relative to the aperture 4 and also define a junction between the inner surfaces 6, 7. With respect thereto it should be noted here that the ends of the elastic strap 8 can alternatively be connected to connection points 10 at portions of the body 2 adjacent to the aperture 4. Accordingly the strap 8 extends through the aperture 4 and comprises a first surface 8a facing the first inner surface 6 at the head portion 2a of the body 2 and a second surface 8a facing the second inner surface 7 at the inner side of the part-ring portion 2b of the body 2.

The length of the strap 8 between its both ends is greater than the distance between the connections points 10 whereby the elastic strap 8 obtains a curved or bent shape and in particular forms essentially a part-circle.

FIGS. 1 and 4a shows the strap 8 in a first position wherein the strap 8 is spaced from both the first and second inner surfaces 6, 7. However, the connection points 10 are positioned and the length of the elastic strap 8 between its both ends is dimensioned so that in the first position the distance between the strap 8 and the first inner surface 6 at the head portion 2a of the body 2 is several times larger than the distance between the strap 8 and the second inner surface 7 at the part-ring portion 2b of the body 2. So, in its first position as shown in the FIGS. 1 and 4a, the strap 8 is arranged adjacent to the part-ring portion 2b of the body 2 and causes the definition of a first aperture cross-section area which is limited and encircled by the first inner surface 6 at the head portion 2a of the body 2 and the first surface 8a of the strap 8. During use of the penile constriction ring with the strap 8 in its first position according to the FIGS. 1 and 4a, the penis is to be pushed through the aperture 4 in the first aperture cross-section area i.e. between the inner surface 6 at the head portion of the body 2 and the first surface 8a of the strap 8. According to the embodiment shown in FIG. 4a, the first aperture cross-section area has essentially the shape of an at least approximate circle which is shown in a dotted line and denoted by reference numeral "4.1" in FIG. 4a.

Further, according to the embodiment shown in the FIG. 4 the aperture 4 in total (defined and limited by both the first inner surface 6 at the head portion 2a and the second inner surface 7 at the inner side of the part-ring portion 2b) has essentially the shape of an at least approximate circle, too; this circle, which is shown in a dotted line together with the circle 4.1 in an extra schematic sketch in FIG. 4a in addition to the illustration of the penile constriction ring and denoted by reference numeral "5", is larger than the circle 4.1 defining the first aperture cross-section area. FIG. 4a shows two further dotted lines C and X running in parallel and spaced form each other, wherein line C coincides with the diameter of the circle 5 which essentially defines the aperture 4 in total and line X coincides with the diameter of the circle 4.1 which essentially defines the first aperture cross-section area. Moreover, it is to be noted that according to the embodiment shown in embodiment FIG. 4a, the connection points 10 are arranged close to line X or intersected by line X.

The fact, that the length of the elastic strap 8 between its both ends is greater than the distance immediately between both the connection points 10, results not only in that the strap 8 obtains a curved or bent shape but also in that an internal upsetting pressure occurs within the strap 8 along its lengthwise direction whereby the elastic strap 8 is based beyond a (not shown) dead point to the first position according to FIG. 4a. In addition to the described first position the elastic strap 8 can alternatively be brought into a second position shown in FIG. 4d wherein the FIGS. 4b and 4c schematically illustrate the movement of the strap 8 from the first position to the second position. Before changing from the first position of FIG. 4a to the second position of FIG. 4d, the elastic strap 8 is to be moved from the part-ring portion 2b of the body 2 away towards the first inner surface 6 at the head portion 2a of the body 2; this is to be done by the user by exerting a manual force which is schematically indicated by the arrow M in FIG. 4b. During said movement, the internal upsetting pressure in the elastic strap 8 is increased. After having passed the dead point which lays in the center region of the aperture 4, the internal upsetting pressure then forces the elastic strap 8 to continue moving towards the second position without the user's further aid; this operational state is shown in FIG. 4c wherein the force created by the internal upsetting pressure is indicated by the arrow F. In the shown embodiment, the connections points 10 are positioned and the length of the strap of its both ends is dimensioned so that the strap 8 in its second position shown in FIG. 4d essentially contacts the first inner surface 6 at the head portion 2a of the body 2 and, thus, seems to disappear. As it becomes further clear from FIG. 4d, after the strap 8 has reached its second position a second aperture cross-section area is defined which is limited and encircled by the second inner surface 7 at the inner side of the part-ring portion 2b of the body 2 and the second surface 8b of the strap 8. According to the embodiment shown in FIG. 4d, the second aperture cross-section area has essentially the shape of an at least approximate circle which is shown in a dotted line and denoted by reference numeral "4.2" in FIG. 4d. In addition to the illustration of the penile constriction ring, FIG. 4d further includes a schematic sketch which also shows said circle 4.2 defining the second aperture cross-section area in comparison with the circle 4.1 depicted by a dotted line and defining the first aperture cross-section area of FIG. 4a. A comparison in between the FIGS. 4a and 4d and also between the circles 4.2 and 4.1 in FIG. 4d shows that the second aperture cross-section area of FIG. 4d is larger and wider than the first aperture cross-section area of FIG. 4a. Consequently, the smaller first aperture cross-section area provides a tight fit, whereas the larger second aperture cross-section provides a more comfort fit.

It should be noted here that of course the aperture 4 and the first and second aperture cross-section areas can also have an alternative shape other than the shape of an at least approximate circle according to the above described embodiment. For example, according to an alternative embodiment, the aperture 4 can have essentially the shape of an at least approximate ellipse as indicated in FIG. 5 which is a schematic sketch consisting only of simple lines which represent the relevant elements. Since an ellipse has two orthogonal diameters of different length, i.e. a longer transverse diameter and a shorter conjugate diameter, FIG. 5 shows a first virtual line $E_1$ with which the transverse diameter coincides and a second virtual line $E_2$ with which the conjugate diameter coincides. Further shown in FIG. 5 is the virtual line X which is already known from FIG. 4 and includes both the connection points 10. According to the modified embodiment of FIG. 5, the virtual line X is spaced from and extends parallel to the virtual line $E_2$ and, thus, the conjugate diameter. Moreover, the ellipse can preferably dimensioned so that the second aperture cross-section area, wherein the elastic strap 8 is in its second position adjacent or close to the first inner surface 6 at the head portion 2a of the body 2 corresponding to the state shown in FIG. 4d, has essentially a shape of an at least approximate circle, wherein the difference of the length between the transverse diameter along the virtual line $E_1$ and the conjugate diameter along the virtual line $E_2$ essentially corresponds to the width of the strap 8.

Moreover, as it becomes clear from the FIGS. 1 to 4, in the shown embodiment the body 2 and the strap 8 form a common integral unit.

Figure 3:
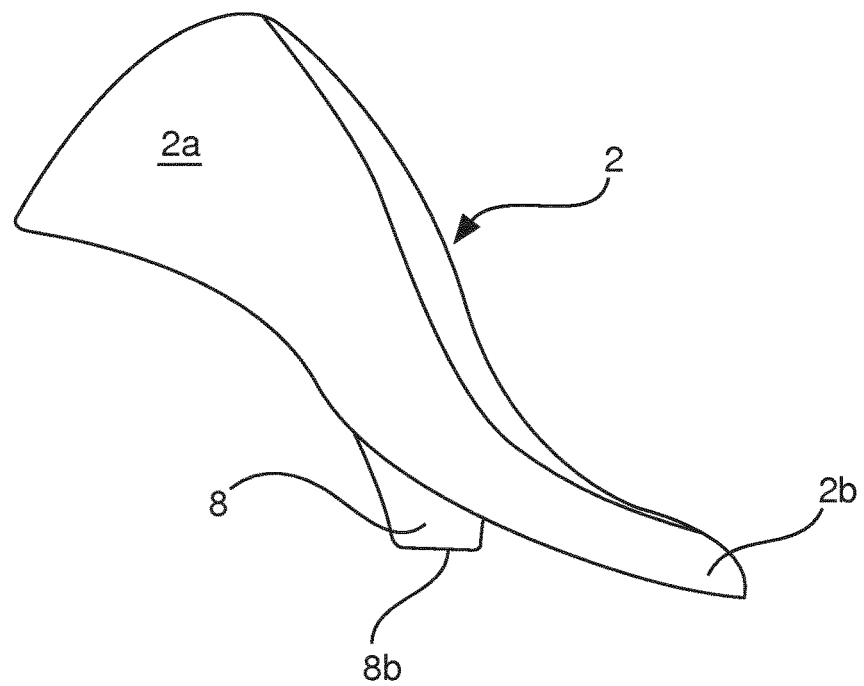
FIG. 3 is another side view of the penile constriction ring of FIG. 1 with a part-ring portion of the body shown in a stretched state.

Further, in the shown embodiment, not only the strap 8, but also the part-ring portion 2b of the body 2 is made of elastic material so that it can be stretched and bent e.g. for placing behind the testicals. FIG. 3 shows as an example the part-ring portion 2b in a bent and stretched state.

Figure 2:
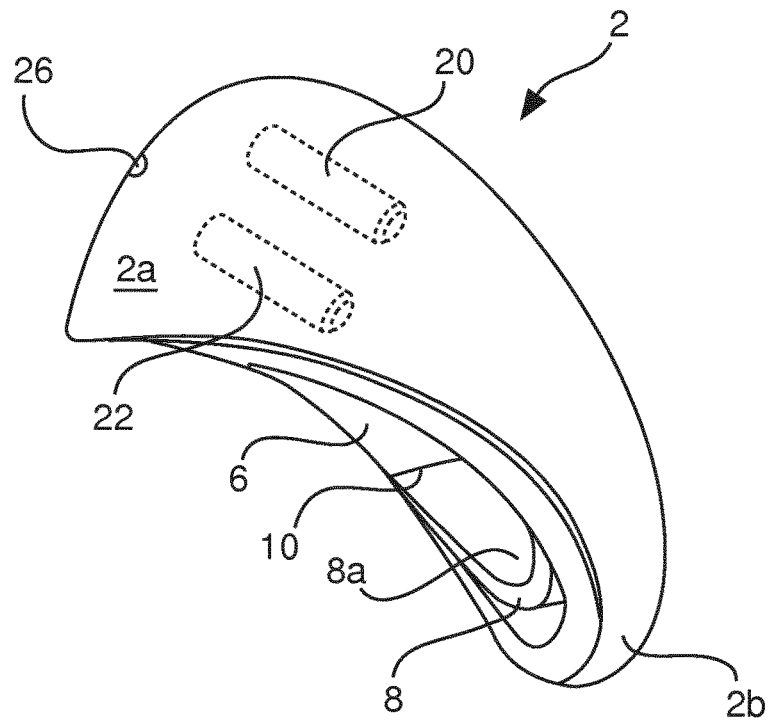
FIG. 2 is a perspective side view of the penile constriction ring of FIG. 1 with a vibrating means and a battery additionally shown in dotted lines.

As further shown in dotted lines in FIG. 2, the head portion 2a of the body 2 includes a vibration means 20 adapted to transfer vibrations to an outer surface of at least the heads portion 2a or even of the whole body 2. During use of the penile constriction ring, the head portion 2b can be arranged so as to head towards a female organ like the clitoris so that the head portion 2a may hit this organ with each move and transfer the vibrations from the vibrations means 20. As also shown in dotted lines in FIG. 2 the head portion 2a additionally includes a battery 22 for supplying the vibration means 20 with electrical power. For activating, controlling and deactivating the vibration means 20, switches are provided whose buttons are arranged on the outer surface of the head portion 2a as shown in FIG. 1. At the free end of the head portion 2a there is provided an electrical connector 26 for connection of an electrical cable (not shown) for charging the battery 22.

Finally, it should be noted that at least partly the surface of the body 2 and/or the strap 8 and preferably the whole body 2 and the whole strap 8 are at least made of soft silicone material.

The invention claimed is:

1. A penile constriction device comprising
    a body including an aperture for surrounding a penis
    an elastic strap having opposing ends each of which is connected to a corresponding connection point at a portion of the body adjacent to the aperture
    wherein the connection points are positioned opposite to each other relative to the aperture and the length of the strap between its ends is greater than the distance between the connection points so that the strap is able to be optionally brought into a first strap position wherein the strap curves toward one side of the aperture or a second strap position wherein the strap curves toward an opposite side of the aperture and
    wherein in the first strap position the strap and the aperture define a first aperture cross-section area for receiving a penis, and in the second strap position the strap and the aperture define a second aperture cross-section area for receiving the penis which is larger than the first aperture cross-section area.

2. The device according to claim 1, wherein the connection points are positioned and the length of the strap is dimensioned so that the strap is essentially spaced from the inner edge of the aperture in the first strap position and essentially contacts the inner edge of the aperture in its first the second strap position.

3. The device according to claim 1 wherein both the first and second aperture cross-section areas have a shape of a circle or that approximates a circle, wherein the diameter of the second aperture cross-section area is larger than the diameter of the first aperture cross section area.

4. The device according to claim 1, wherein the aperture has a shape of a circle or that approximates a circle, and the connection points are positioned at a virtual straight line spaced apart from the diameter of the circle of the aperture.

5. The device according to claim 1, wherein the aperture has a shape of an ellipse or approximating an ellipse and has a transverse diameter and a conjugate diameter, and the connection points are positioned at a virtual line spaced from the conjugate diameter of the ellipse.

6. The device according to claim 5, wherein the virtual line extends parallel to the conjugate diameter of the ellipse.

7. The device according to claim 5, wherein the transverse and conjugate diameters of the ellipse are dimensioned so that the second aperture cross section area has essentially a shape of a circle or that approximates a circle.

8. The device according to claim 7, wherein the difference of the length between the transverse diameter and the conjugate diameter of the ellipse essentially corresponds to the width of the strap.

9. The device according to claim 1, wherein the body and the strap commonly form an integral unit.

10. The device according to claim 1, wherein the body comprises a part-ring portion limiting the aperture.

11. The device according to claim 10, wherein the part-ring portion is elastic and stretchable.

12. The device according to claim 1, wherein the body comprises an extended portion which includes vibration means adapted to transfer vibrations to an outer surface of at least the extended portion of the body.

13. The device according to claim 12, wherein the extended portion of the body further includes a battery and an electrical connector for connection of an electrical cable for charging the battery.

14. The device according to claim 1, wherein the body or the strap is at least partly made of soft silicone material.

15. A penile constriction device comprising:
a body defining an aperture having a cross-section area sized to surround a penis; and
an elastic strap having opposing ends, each of which is connected to the body at one of two strap connection points that are at or adjacent to opposing sides of the main aperture, wherein the length of the strap between its opposing ends is greater than the length of a virtual straight line between the two strap connection points and wherein the strap can be elastically moved between a first strap position wherein the strap curves toward one side of the aperture and a second strap position wherein the strap curves toward an opposite side of the aperture;
wherein when the elastic strap is in the first strap position, the aperture and the strap define a first aperture cross-section area for receiving the penis, and when the strap is in the second strap position, the aperture and the strap define a second aperture cross-section area for receiving the penis that is larger than the first aperture cross-section area.

16. The device according to claim 15, wherein the connection points are positioned and the length of the strap is dimensioned so that, when the strap is in the first strap position the strap is essentially spaced apart from the inner edge of the aperture, and when the strap is in the second strap position the strap essentially contacts the inner edge of the aperture.

17. The device according to claim 15 wherein both the first and second aperture cross-section areas have essentially a shape of a circle or that approximates a circle, wherein the diameter of the second aperture cross-section area is larger than the diameter of the first aperture cross section area.

18. The device according to claim 15 wherein the aperture has essentially a shape of a circle or that approximates a circle, and the connection points are positioned on a virtual straight line spaced apart from the diameter of the circle of the aperture.

19. The device according to claim 15, wherein the aperture has essentially a shape of an ellipse or that approximates an ellipse and has a transverse diameter and a conjugate diameter, and the connection points are positioned on a virtual straight line spaced apart from the conjugate diameter of the ellipse.

20. The device according to claim 15, wherein the virtual line extends parallel to the conjugate diameter of the ellipse.

* * * * *